United States Patent [19]
Handler et al.

[11] Patent Number: 5,218,956
[45] Date of Patent: Jun. 15, 1993

[54] HAND-HELD ORAL IRRIGATING DEVICE

[75] Inventors: Michael D. Handler, Weston, Conn.; Burt Shulman, Pleasant Valley, N.Y.; Scott Salmon, Leonia; Scott Eagle, Long Branch, both of N.J.

[73] Assignee: Hydrodent Laboratories, Inc., Woodbridge, N.J.

[21] Appl. No.: 786,512

[22] Filed: Nov. 1, 1991

[51] Int. Cl.⁵ .............................................. A61H 9/00
[52] U.S. Cl. ...................................... 128/66; 604/19; 433/80
[58] Field of Search ...................... 128/66; 604/19, 22, 604/82–85; 433/80, 88

[56] References Cited

U.S. PATENT DOCUMENTS

| | | | |
|---|---|---|---|
| 3,452,746 | 7/1969 | Shanhouse | 128/66 |
| 3,777,746 | 12/1973 | Kwok | 128/66 |
| 4,668,190 | 5/1987 | Overmyer | 433/80 |
| 4,941,459 | 7/1990 | Mathur | 128/66 |
| 4,979,503 | 12/1990 | Chernack | 128/66 |
| 5,095,893 | 3/1992 | Rawden, Jr. | 128/66 |

*Primary Examiner*—Stephen C. Pellegrino
*Assistant Examiner*—Michael Rafa
*Attorney, Agent, or Firm*—Cohen, Pontani, Lieberman, Pavane

[57] ABSTRACT

An oral irrigator device is formed of an adapter mountable in interposed relation between a supply pipe of treatment liquid, generally water, and a shower head, a user-graspable handpiece, and a flexible liquid-communicating hose connecting the adapter and handpiece. A rotatable turbine within the adapter generates, from the continuous-flow stream of treatment liquid from the supply pipe, a pulsating stream of the liquid for delivery to the handpiece through a normalizing flow regulator and the flexible connecting hose. In the handpiece, the pulsating stream is separated into a primary stream for discharge through an appliance head carried on the handpiece and a secondary stream that is directed into an expansion chamber partially bounded by an elastic diaphragm which separates the chamber from a storage reservoir for a flowable medicament. As the expansion chamber fills with liquid from the secondary pulsatile stream, the diaphragm expands into the reservoir, thus applying pressure on the stored medicament which is ejected from the reservoir for mixture with the primary stream. The pressure of the primary stream is reduced relative to the secondary stream pressure so as to facilitate even mixing of the ejected medicament and primary pulsatile liquid streams.

19 Claims, 11 Drawing Sheets

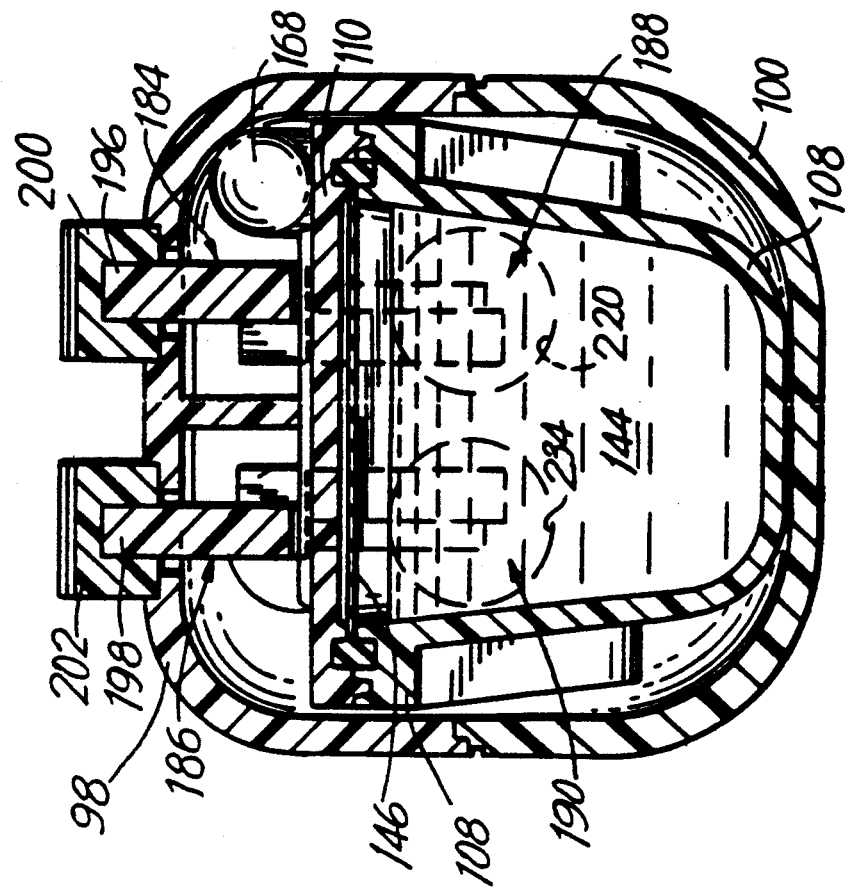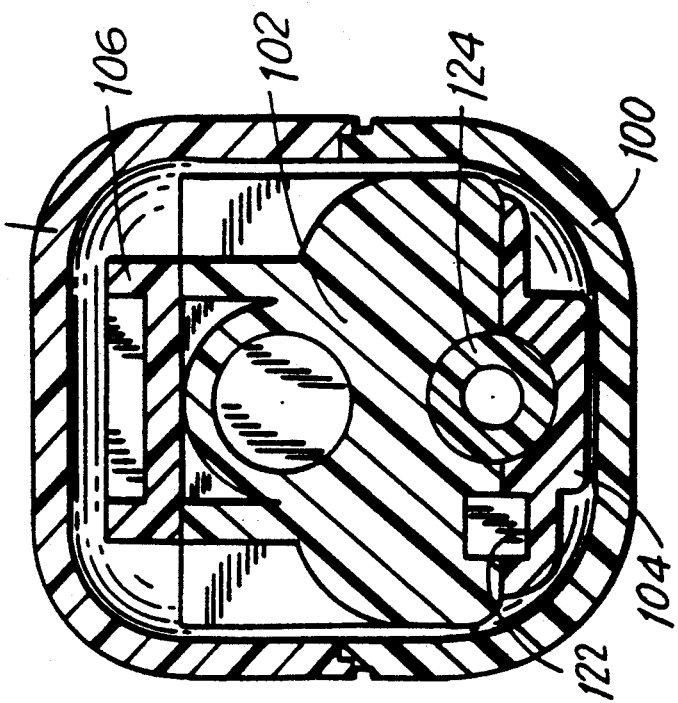

HAND-HELD ORAL IRRIGATING DEVICE

FIELD OF THE INVENTION

The present invention is related to devices for operatively producing and discharging a pulsatile stream of a fluid, generally a liquid, from an incoming continuous-flow source or supply of the fluid. It is more particularly directed to such a device which is adapted for use in oral irrigation, as for example to cleanse the teeth and stimulate the gums of the user, whereby the pulsatile liquid is mixed by the device with an additive at a predetermined constant, and optionally user-selectable, ratio of additive to liquid that is automatically dynamically maintained irrespective of rapid or unanticipated surges and fluctuations in the pressure and flow rate of the incoming liquid.

BACKGROUND OF THE INVENTION

Oral irrigators for use in the environment of a bathtub or shower stall, that include a hand-held, user-manipulatable applicator for discharging a pulsating stream of the treatment liquid, typically water, and which are driven solely by an incoming continuous-flow (i.e. non-pulsatile) stream of the liquid are known in the art. Such a device, including a turbine-incorporating adapter mounted between the water feed pipe and a conventional shower head for generating the pulsatile flow, is for example disclosed in U.S. Pat. No. 4,564,005 to Marchand.

A particularly desirable operating aspect of such oral irrigators is their ability to mix, with the pulsatile stream of water they discharge, an additive such as a medicament suitable for maintaining or enhancing the health of the teeth and/or gums of the user. In the Marchand device, this functionality is provided by including in the handpiece a cage-like compartment for holding a solid-form additive over which the pulsatile water stream is directed to melt the additive and thereby blend the additive into the discharged flow emanating from the handpiece. This manner of mixing necessarily and disadvantageously results in inconsistent and virtually unpredictable concentrations or ratios of additive to water in the resulting mixture, thereby greatly reducing, or virtually eliminating, the consistent effectiveness of the additive on the user's teeth and/or gums. Such an arrangement also significantly limits the user's ability to use a highly concentrated form of the additive—so as to correspondingly increase the period of irrigator use before which the additive in the handpiece must be replenished. The lack of real and effective control over the mixing ratio presents the possibility and risk of injury to the gums or teeth should the resulting mixture include a dangerously high concentration of the additive. Still another deficiency in the Marchand apparatus is the inability to automatically and effectively normalize or otherwise regulate and control, within predeterminately safe and consistently-maintained limits optimized for user-comfort, the pressure and volumetric flow rate of the water stream that is fed to the device from the feed source and from which the pulsatile discharge stream is generated.

An improved arrangement for dispensing a controllable ratio of an additive or medicament into a stream of treatment liquid for pulsatile discharge from an oral applicator device is disclosed in U.S. Pat. No. 4,979,503 to Chernack, commonly-owned herewith. In the Chernack irrigator, medicament in a preferably concentrated liquid form is ejected, for mixture with a pulsatile stream of the treatment liquid, from a storage reservoir by a gear pump that is directly operated by a turbine which generates the pulsatile flow from the incoming continuous-flow stream. The volume of ejected medicament concentrate for mixture with the treatment liquid is therefore directly related to, and is automatically dynamically adjusted in accordance with, the treatment liquid flow, seemingly assuring a substantially constant volumetric ratio of medicament to treatment liquid in the resulting mixture for discharge from the irrigator handpiece. In practice, however, resistance to such forced mixing of the ejected medicament and treatment liquid streams has been found to result in a variety of dynamic impediments to the attainment of a relatively constant ratio of medicament to treatment liquid in the discharged pulsatile stream.

OBJECTS OF THE INVENTION

It is accordingly the desideratum of the present invention to provide a device for generating a pulsatile stream of treatment liquid while overcoming the various deficiencies and drawbacks of prior art devices.

It is a particular object of the invention to provide such a liquid-powered, hand-held oral irrigating device in which a medicament is mixed with a treatment liquid for discharge of a pulsatile stream of medicated treatment liquid from the device.

It is another object of the invention to provide such a device in which the medicament is ejected from a storage reservoir for mixing with the treatment liquid at a substantially constant ratio or predetermined progression of ratios.

It is further object of the invention to provide such a device in which the ejection of medicament from the reservoir is automatically dynamically adjusted in accordance with and to accommodate surges, fluctuations and changes in the pressure and flow rate of the treatment liquid.

Yet another object of the invention is provide such a device in which the ejected medicament fully mixes with the treatment liquid at a substantially constant ratio.

A still further object of the invention is to provide such a device in which the volumetric ratio of medicament to treatment liquid in the resulting medicated treatment liquid pulsatile stream is selectively-adjustable by the user.

It is an additional object of the invention to provide such a device which automatically normalizes the pressure and/or volumetric flow rate of the time-varying incoming continuous flow stream of treatment liquid to a safe and consistent predetermined range that is optimized for user comfort.

It is a further object of the invention to provide such a device which is operatively connectable to a conventional shower head water feed pipe so as to derive the device-operating continuous flow stream of treatment liquid from the stream of water normally directed to the shower head without significant effect on the pressure or flow rate of water being fed to and discharged outwardly from the shower head.

Another object of the invention is to provide such a device that is relatively low in cost and which may be readily and economically manufactured from conventionally-available parts and materials utilizing well-known techniques.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein similar reference characters denote similar elements throughout the several views:

FIG. 11 is a sectional view taken along the lines 11—11 in FIG. 9; and

FIG. 12 is a sectional view taken along the lines 12—12 in FIG. 12.

DETAILED DESCRIPTION OF THE PREFERRED EMBODIMENT

Figure 1:
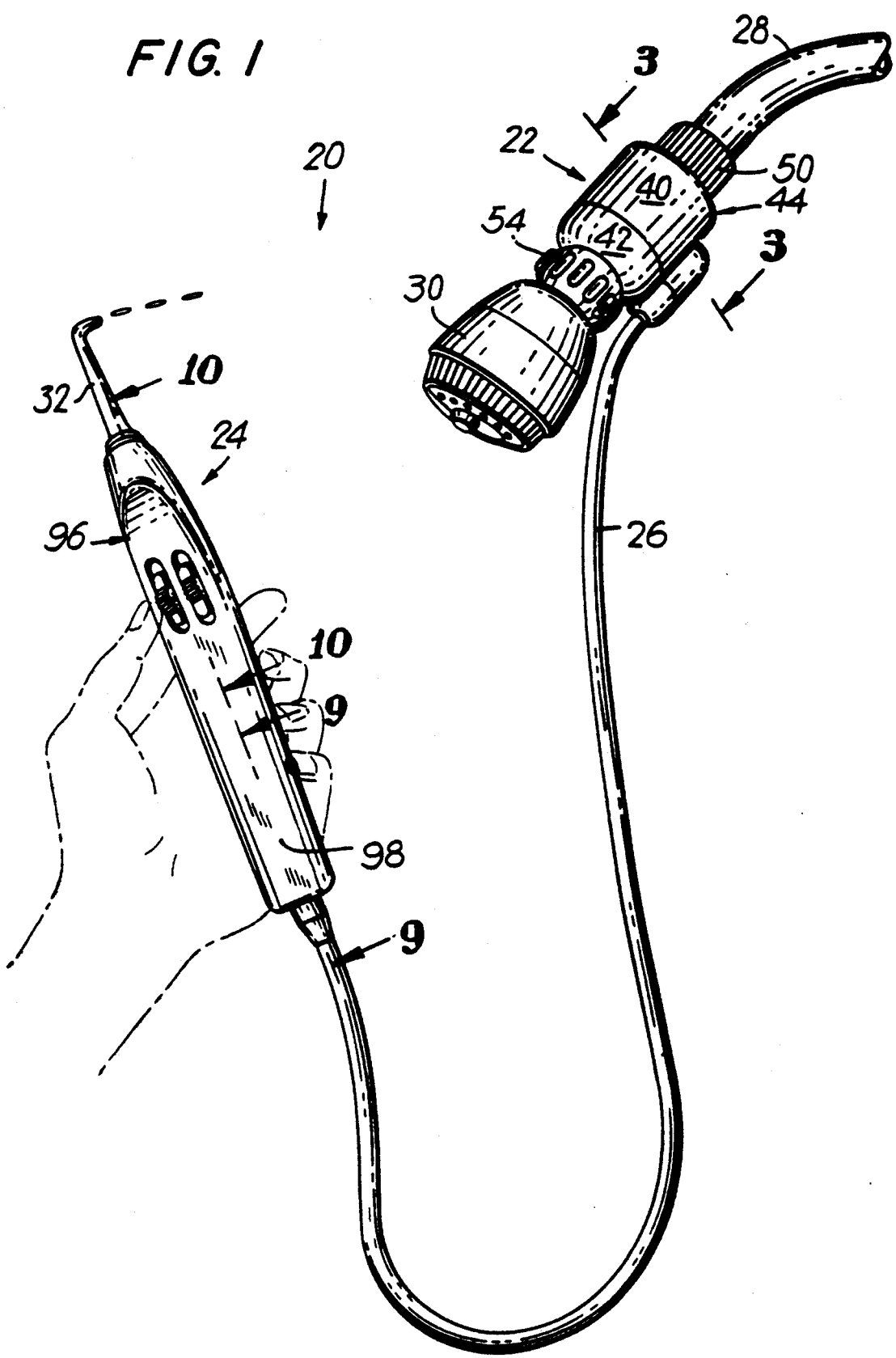
FIG. 1 is a perspective view of a hand-held oral irrigating device constructed in accordance with the present invention and depicted in operative association with an otherwise-conventional shower head installation.
Figure 2:
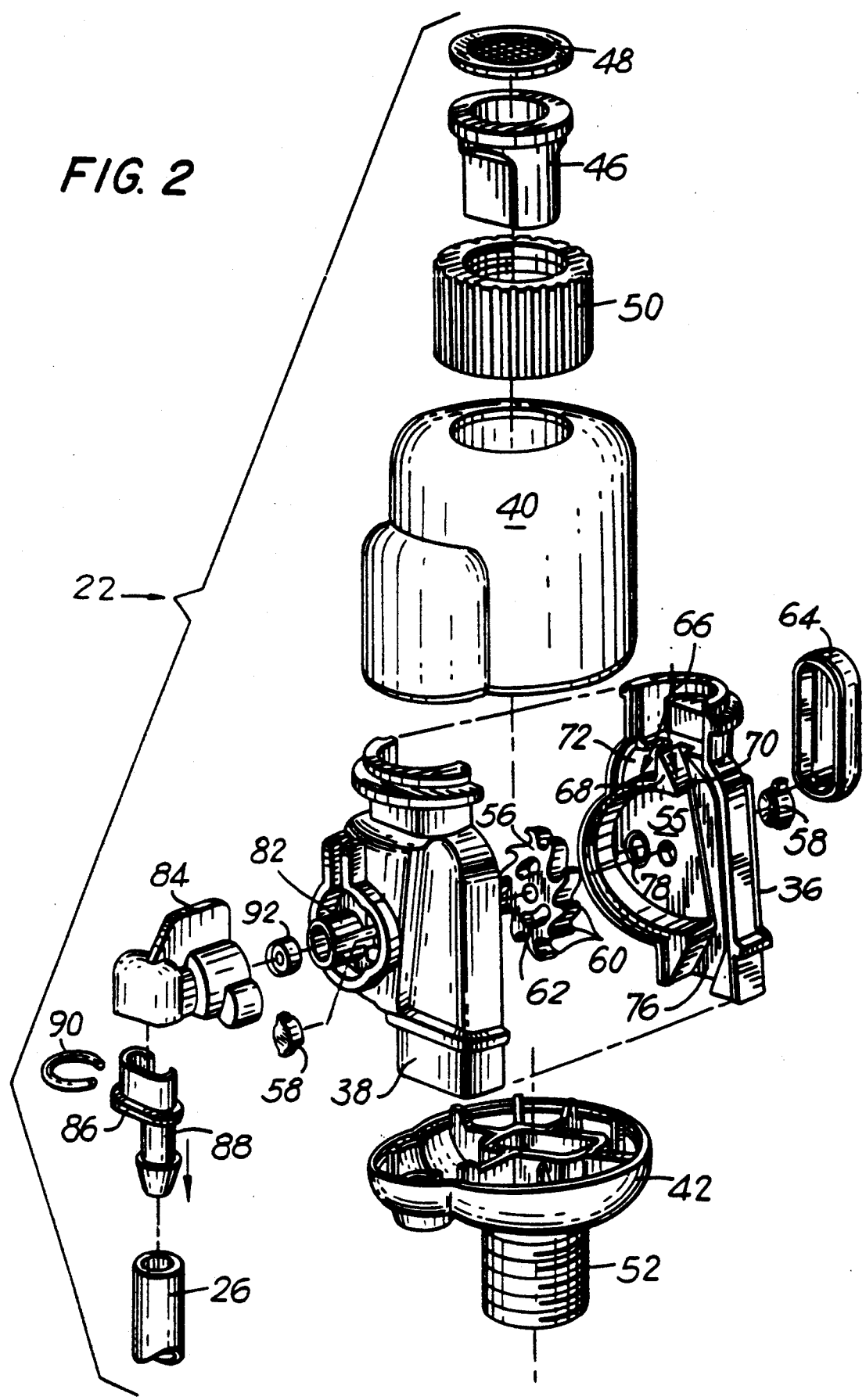
FIG. 2 is an elevated perspective, exploded view of a preferred embodiment of a shower head adapter that forms a part of the oral irrigating device of the invention.
Figure 3:
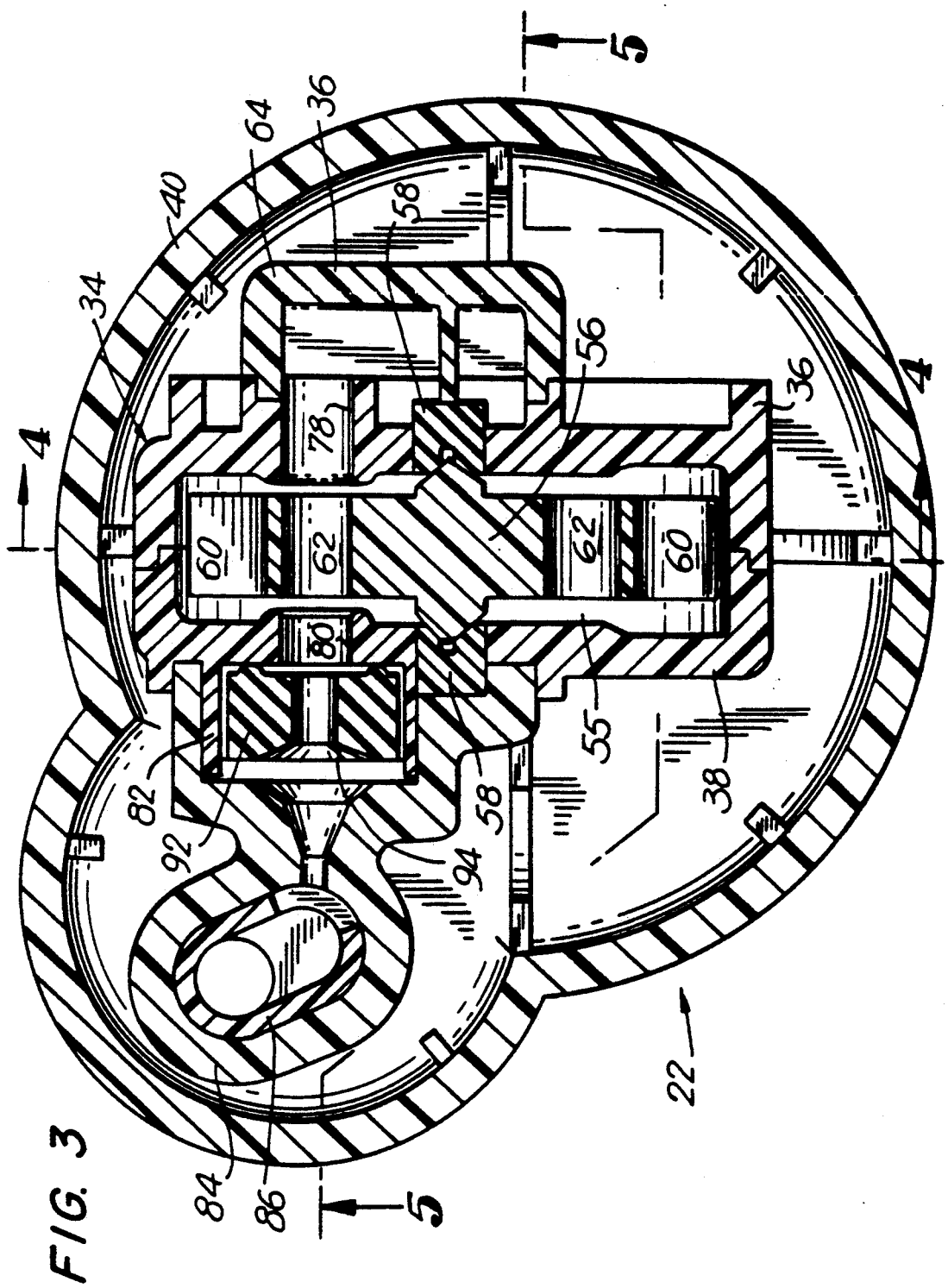
FIG. 3 is a sectional view taken along the lines 3—3 in FIG. 1.

The present invention is directed to an oral irrigating device which, when used in conjunction with an input stream of continuous flow treatment liquid, outputs a pulsating flow of the liquid and, more particularly, of a medicated liquid formed of a substantially constant-ratio mixture of the treatment liquid and a medicament or the like. As used herein, the term "continuous flow" is intended to distinguish a flow of liquid at a substantially constant—or at least a slowly or irregularly varying—volumetric rate from the pulsatile flow produced by and output from the device of the present invention. Moreover, it is generally contemplated, particularly with respect to the primary intended utility of the invention as herein disclosed, that the treatment liquid will comprise water and the following description may therefore refer, from time to time, to that liquid as water. It should, however, be understood that no limitation on the scope of the present invention is intended by such references, and that the treatment liquid used in conjunction with the inventive device may accordingly comprise any liquid deemed suitable and appropriate to the intended use of the invention.

In addition, the use herein of the term "medicament" for the additive with which the treatment liquid is operatively mixed for discharge from the inventive device is similarly intended to be understood in a broad and non-limiting manner. In the preferred and most generally contemplated utility of the invention—i.e. in a hand-held, user-manipulatable oral irrigator for selectively directing or applying a discharged stream of pulsating liquid onto the teeth and gums or other regions of the user's mouth—the medicament may for example comprise a concentrated liquid that, when applied to the teeth and gums, facilitates the removal of plaque and promotes gingival health. Nonetheless, those skilled in the art will recognize that the so-called medicament may be virtually any flowable fluid, generally in liquid form, which the user desires to mix with or add to the treatment liquid for the contemplated use. Thus, by way of example and not limitation, the medicament may comprise a mouthwash, or dentifrice, or cleaner, or plaque remover, or flavorant, or prescription product, or some predetermined combination thereof. It should further be recognized and appreciated that the ability of the inventive device to maintain a substantially constant volumetric ratio of medicament to treatment liquid in the pulsatile output stream that is discharged from the device advantageously permits the use of medicaments which are stored in known concentrations or are otherwise most preferably utilized or require, for most effective use, particular dilution ratios or treatment amounts or the like. Thus, by way of illustration a medicament may be stored in the internal reservoir of the inventive device in a highly concentrated form which could not be comfortably or effectively directly ingested or applied by the user, the construction and operation of the inventive device assuring that only an appropriate and effective dilution of the stored concentrate will be discharged in a pulsatile stream through a mounted appliance head or tip as will hereinafter be described.

It will also be appreciated that a noteworthy and advantageous feature of the inventive irrigating device lies in its being powered solely by the incoming liquid stream so as to require no external or otherwise stored source(s) of energy for operating the device. The further ability of the inventive device to automatically mix with the pulsatile liquid stream generated from the incoming flow—at an adjustably-predetermined and, most significantly, substantially constant volumetric ratio to the pulsating liquid—a preferably concentrated medicament or additive that is stored in the applicator housing is another important and advantageous feature of the present invention.

An oral irrigator constructed in accordance with the invention and identified in FIG. 1 by the general reference numeral 20 is formed of an adapter 22, a user-held and manually-manipulatable handpiece 24, and a pulsed liquid conduit-defining flexible hose 26 connecting the adapter and handpiece. The adapter 22 is mounted supportedly on or to the generally-fixed feed or supply pipe 28 through which liquid, typically water, is fed to a conventional shower head 30, the adapter being positioned in bridgingly interposed relation between the pipe 28 and the shower head 30 which, in the absence of the inventive apparatus, is normally mounted directly to the fixed supply pipe 28.

As will hereinafter become apparent, the adapter 22 operatively functions, first, to communicate virtually the entirety of the stream of liquid that flows through and from the supply pipe 28 to the shower head 30 for delivery from the head. Moreover, the adapter operatively generates, from the incoming liquid stream, a pulsating, normalized stream of the liquid—within a suitable and predetermined range of flow rates—that is output through the flexible hose 26 and thereby fed to the handpiece 24. In the handpiece, the pulsating liquid flow is selectively mixable with a concentrated medicament or the like and the resulting pulsatile mixture is ejected through an appliance head or tip 32 or the like for irrigating or otherwise treating the user's mouth or a particular part or region thereof.

Figure 4:
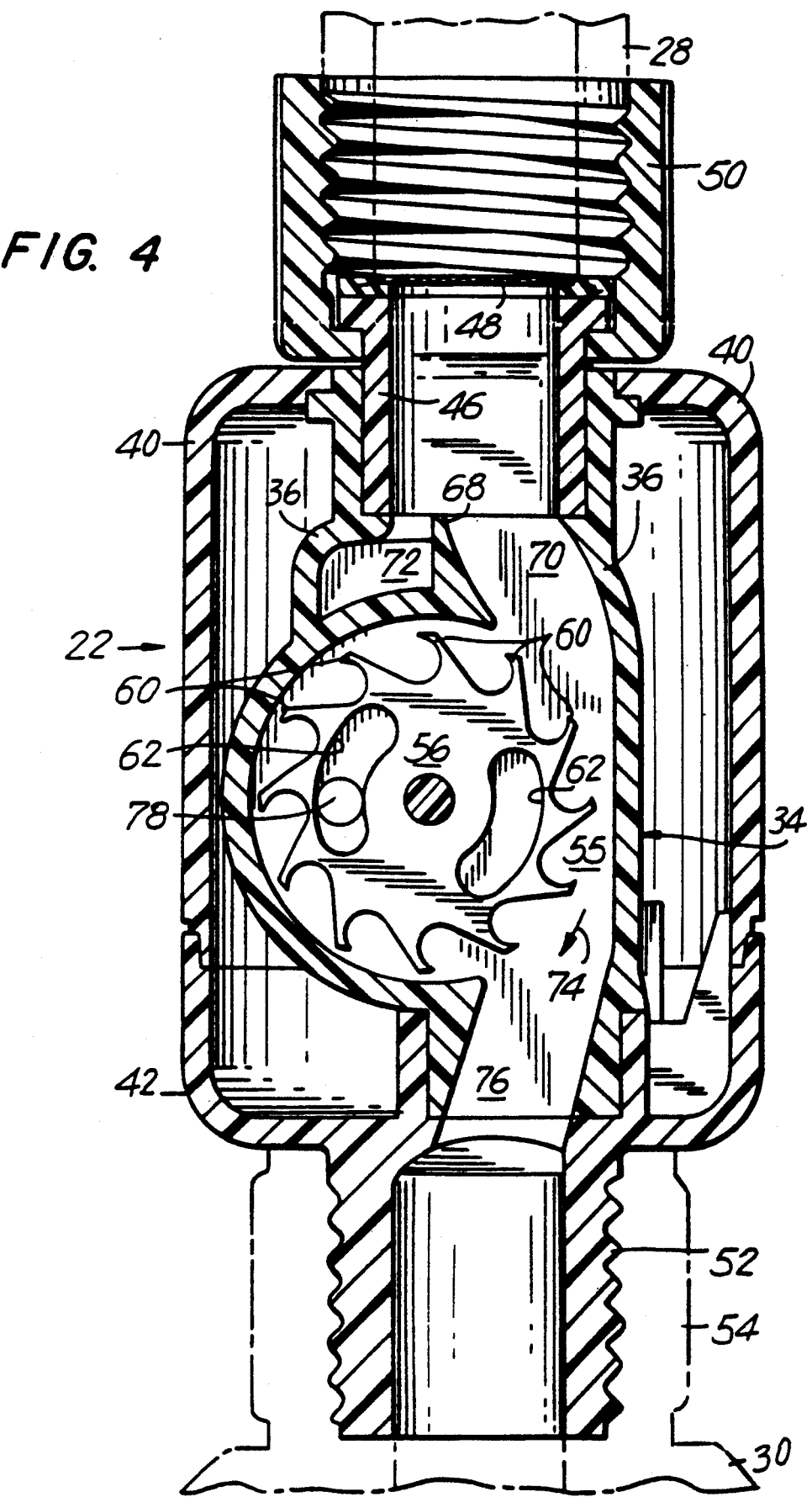
FIG. 4 is a sectional view, partly broken away, taken along the lines 4—4 in FIG. 3.
Figure 5:
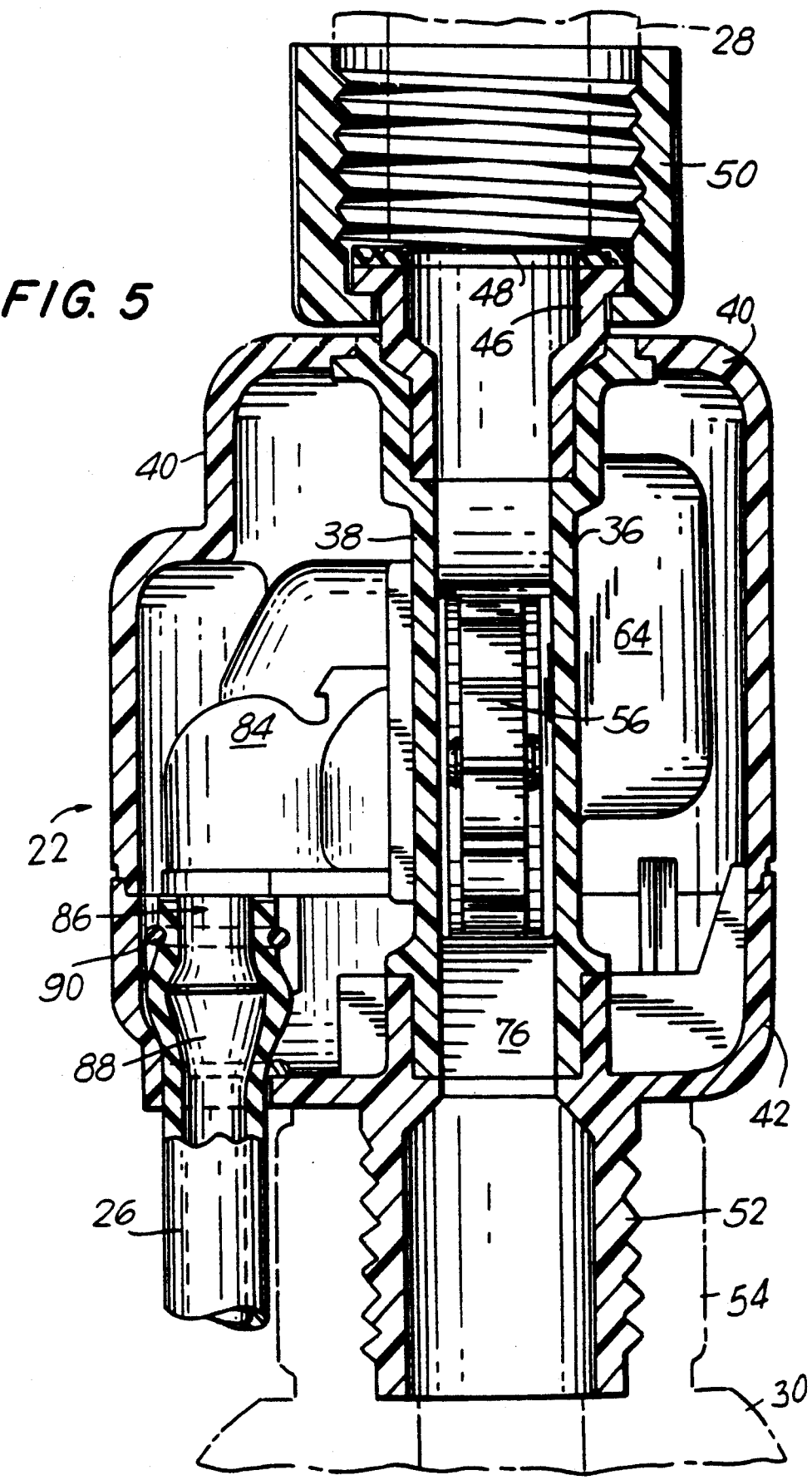
FIG. 5 is a sectional view, partly broken away, taken along the lines 5—5 in FIG. 3.

Details of the individual elements and overall construction of the specific embodiment of the shower head adapter 22 herein disclosed are depicted in FIGS. 2 to 5. As perhaps best seen in the exploded perspective of FIG. 2, the adapter 22 includes a turbine housing 34 formed of liquid-tightly interengaging halves herein referred to, for convenience and ease of description, as the inlet side or part 36 and the outlet side or part 38. An adapter shell 40 and an adapter base 42 cooperatively interengage to define an outer casing 44 that substantially encloses and envelops the turbine housing 34. The supportedly-mounted connection of the adapter 22 to the liquid inlet supply pipe 28 is provided by way of an inlet supply connector element 46 that may be welded or otherwise nonremovably secured or coupled to the turbine housing 34. The element 46, together with an optional screen 48 for which the connector element 46 provides a seat, is in turn secured to the threaded free end of the supply pipe 28 by a correspondingly threaded upper retaining sleeve 50 as seen in FIGS. 4 and 5.

Mounting of the shower head 30 to the adapter 22 may be accommodated by including a hollowed, tubular, liquid-communicating extension 52 on the adapter base 42 and threaded for rotative engagement with a similarly threaded sleeve 54 or the like which typically forms a portion or element of the shower head assembly.

Thus, the adapter 22—supportedly mounted at one end to the supply pipe 28 and itself supporting the shower head 30 at its opposite end—interposingly channels incoming liquid from the pipe 28 to the shower head and, as will now be described, additionally diverts and outputs a pulsating stream of the liquid into the flexible hose 26 for delivery to the handpiece 24.

The inlet and outlet sides 36, 38 of the turbine housing 34 define a liquid receiving and communicating interior space including a generally central chamber 55 within which a disk-like turbine or impeller 56 is mounted for freewheeling rotation on bushings or bearings 58 on the housing halves. The generally circular turbine 56 disk carries a plurality of curved and radially-outwardly projecting blades or wings 60 spaced about its outer periphery and further includes one or more axially-offset apertures 62—two being presently preferred and shown in the drawings—defined in and through the central disk of the turbine. These apertures 62 may, as illustrated, be elongated in the circumferential direction of the turbine disk, although fully circular or otherwise variously-shaped apertures are also within the intended scope of the invention.

The turbine housing 34, and more particularly the inlet half 36 and an associated shunt cover 64 in the adapter embodiment herein shown and described, further defines a split path for liquid fed to the adapter 22 from the supply pipe 28 and entering the turbine housing 34 through the connector element 46. The inlet stream is split, as indicated by the arrow 66 in FIG. 2, by a diversion wall 68 into a first or primary stream (depicted by the right-pointing portion of the arrow 66) that flows through a first channel 70 and a second or subsidiary stream (depicted by the left-pointing portion of the arrow 66) that flows through a second channel 72. The first channel 70 guides the primary stream directly into the central chamber 55 and onto the turbine blades 60 to thereby effect rotation of the turbine 60 in the direction of the arrow 74 (FIG. 4). From the turbine blades 60 and chamber 55 the primary stream exits the chamber through an outlet channel 76 defined in the housing 34 and from which the primary, continuous flow liquid stream is directed through the adapter extension 52 into the shower head 30. In practice, the use of the primary stream to operatively rotate the turbine 60 has been found to reduce the liquid flow from the supply pipe 28 to the shower head 30 by an amount that is substantially insignificant or unnoticeable by the user—on the order, by way of example, of as little as 3 to 5 percent—over that which would flow outwardly from the shower head were it mounted directly to the supply pipe.

The second channel 72—which preferably diverts only a relatively small volumetric portion of the incoming liquid stream from the supply pipe 28—conducts the subsidiary continuous flow stream along a curved path that carries the stream through the shunt cover 64 and, then, through a feed throughbore 78 defined in the inlet side 36 of the turbine housing 34 at an off-axis location aligned with the axial offset of the turbine apertures 62. A pulse channel outlet 80, circumferentially about which is disposed a sleeve-like nipple 82 that unitarily projects from the exterior wall of the turbine housing outlet side 38, is similarly defined in and through the turbine housing part 38 in a location aligned with the axial offset of the turbine apertures 62. Thus, the continuous flow subsidiary stream of liquid is directed by the second channel 72 through the shunt cover 64, through the feed throughbore 78, and interruptedly against the turbine disk wall substantially transverse to its rotational plane at the axially-offset location of the apertures 62. As the turbine 56 is operatively rotated by the continuous flow primary liquid stream, the turbine apertures 62 are successively carried into registry with the feed throughbore 78 and, thereby, into periodically and repetitively aligned registration with the continuous flow subsidiary stream of liquid emanating from the feed throughbore 78, thus generating a pulsating flow of liquid that passes through the turbine apertures 62 and issues from the turbine housing 34 through the correspondingly aligned pulse channel outlet 80 and into the nipple 82.

Redirection of the resulting pulsatile flow of treatment liquid from the pulse channel outlet 80 into and through the flexible hose 26 and, thence, to the handpiece 24 is effected by the combination of a flow control housing 84 that is liquid-tightly mounted to the turbine housing half 38 over the nipple 82 and a pulsed outlet hose connector element 86. The connector element 86 is received at its input end nestedly within the flow control housing 84 and carries, at its outlet end, a suitably-configured extension sleeve 88 over which the end of the flexible hose 26 is secured. A split clamping ring 90 or the like may also be provided, as seen in FIG. 5, about the hose 26 at its engagement with the connector element extension 88 to prevent unintended slippage or disconnection of the hose and to facilitate its liquid-tight attachment to the connector element 86.

Those skilled in the art will appreciate that the pressure and volumetric flow rate of water that is fed from a typical supply pipe 28 to a shower head 30 will often vary over a significant range—both from geographic location to location as well as at or within a single building or house or apartment or bathroom installation—as a function of numerous factors, only some of which are at least somewhat controllable by the user. Such factors include the type and construction of the particular shower head, the state of relative repair (or disrepair) and resulting operational efficiency of the shower head, the operating position(s) of any valves or variable controls on or associated with the shower head and/or the liquid supply line, concurrent uses of water in other parts of the building or apartment, and the water pressure normally or at least currently available from the typically-external source or supply of water. Also significant are continuous, irregular and generally-unpredictable fluctuations in the pressure and volumetric flow rate of water without regard to any of the other causes or bases of such variations. In order to maintain the pulsatile stream of liquid that is fed to the handpiece 24 through the flexible hose 26 within a suitable range of pressure and flow rate and, at the same time, minimize the effect of otherwise uncontrolled, unpredictable and irregular surges or fluctuations in the flow, the inventive device includes an arrangement for effectively normalizing the pulsatile flow of treatment liquid to the handpiece.

Thus, in the embodiment of the oral irrigator 20 herein disclosed, such normalized regulation is provided by a flow regulator element 92. The element 92 is implemented as a disk of flexible material such, for example, as of nitrile rubber which is captively positioned within the sleeve-like nipple 82. The disk 92 has a centrally-defined bore therethrough, for communicating pulsatile liquid from the outlet 80 into the flow control housing 84, and a downstream face 94—i.e. that surface located most remote from the outlet 80—having an inwardly-bowed or generally concave curvature. At and below a relatively low or predetermined flow rate and pressure of the pulsed liquid stream from the outlet 80 the disk 92 remains in its normal or initial configuration and simply passes the liquid flow through its central bore. With increasing pressure or volumetric flow rate of the pulsed liquid stream, however, there is an outwardly-directed flattening of the bowed surface 94 in substantial relation to the increase in pressure, thereby variably and correspondingly decreasing the cross-sectional size of the disk bore and reducing the rate of pulsatile liquid throughflow to the handpiece 24. In this manner, the disk element 92 normalizes the pulsatile flow so as to smooth unintended variations in volumetric flow rate and, more importantly, to regulate and maintain the flow rate of the pulsed stream of treatment liquid being fed to the flexible hose for delivery to the handpiece 24 within predetermined and suitable limits. For purposes of oral irrigation, a flow rate in the range of approximately 240 cc/min. to approximately 450 cc/min. is considered optimal for user comfort and to effectively lift the gum tissue without damaging or otherwise detrimentally affecting the gums. Nevertheless, variations of approximately 15 percent in that optimal range are considered acceptable in the normally intended and contemplated use of the inventive device.

The flow regulator disk element 92 illustrated and described herein is well known in the art and may be implemented with any suitable unit such, by way of example, as the 0.1 gallon/min. flow control disk which is commercially available from Vernay Laboratories Inc. of Yellow Springs, Ohio as Part No. VL3001-379. Other, functionally-similar flow regulators may alternatively be employed as a general matter of design choice. As should also be apparent, the flow regulator 92 may instead be replaced by a pressure regulator device which, although potentially capable of providing enhanced or finer control of the pulsatile stream being fed to the handpiece 24, is somewhat more costly to implement.

Figure 6:
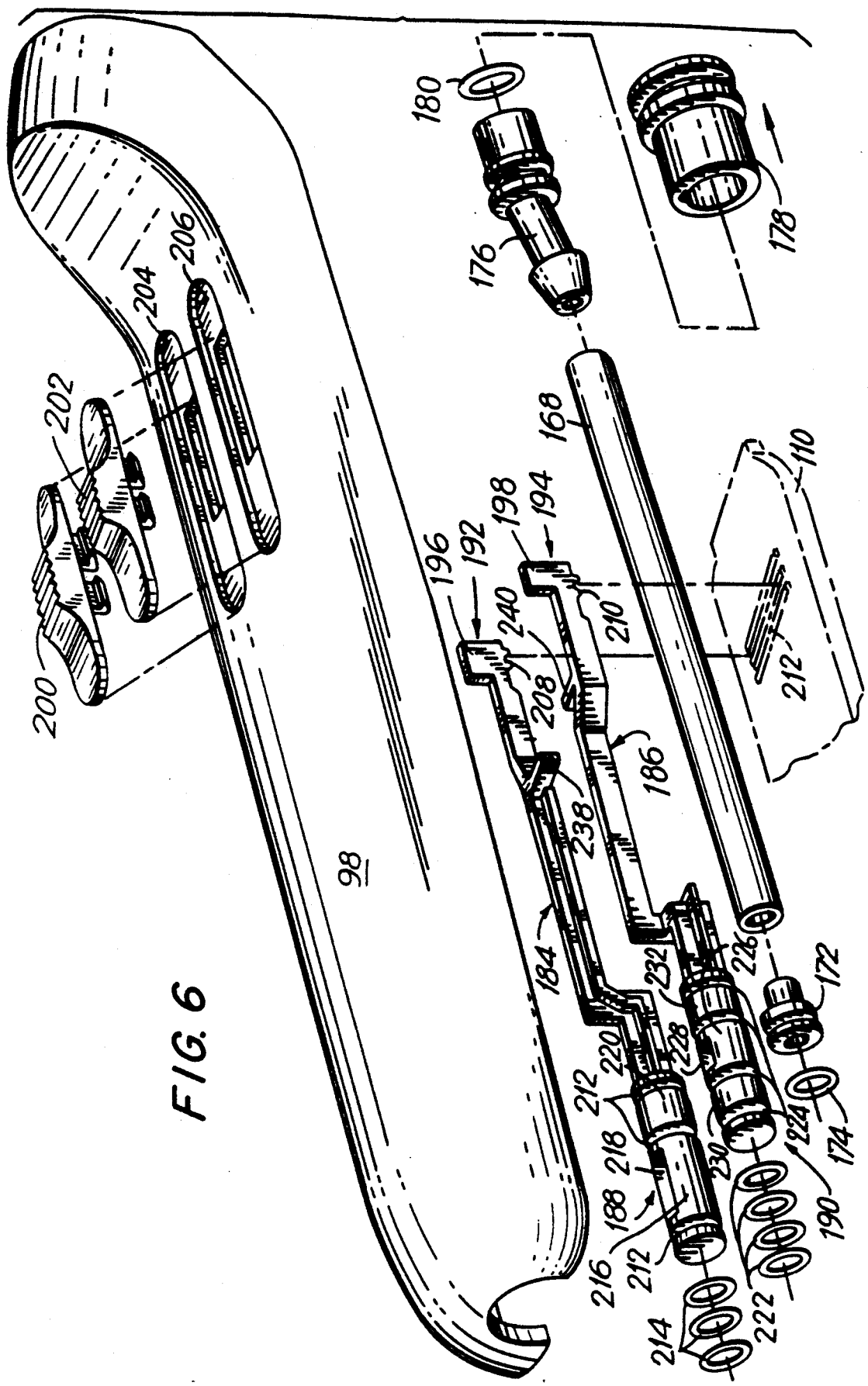
FIG. 6 is an elevated perspective, exploded view of a first portion of a preferred embodiment of a handpiece that forms a part of the oral irrigating device of the invention.
Figure 7:
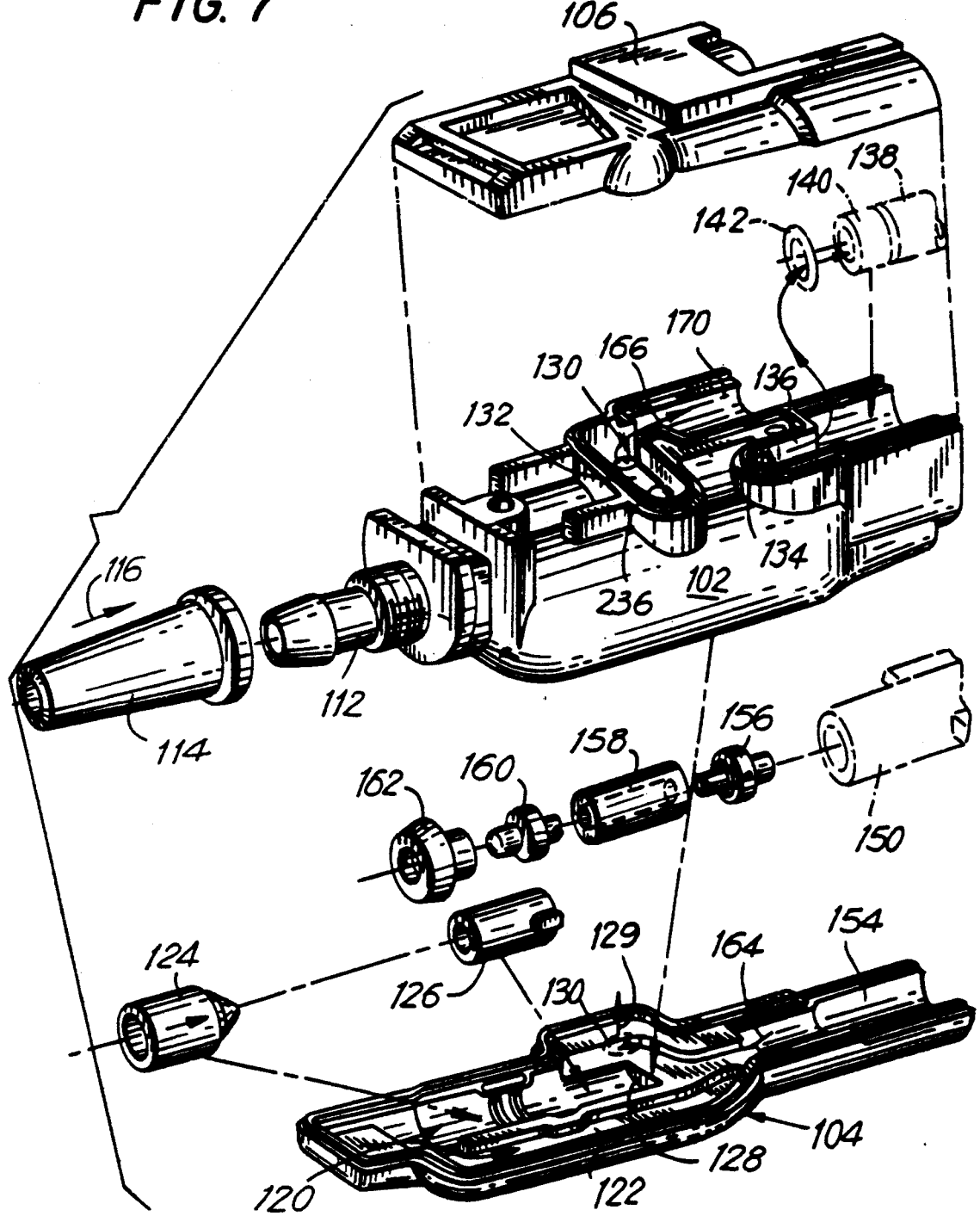
FIG. 7 is an elevated perspective, exploded view of a second portion of the handpiece.
Figure 8:
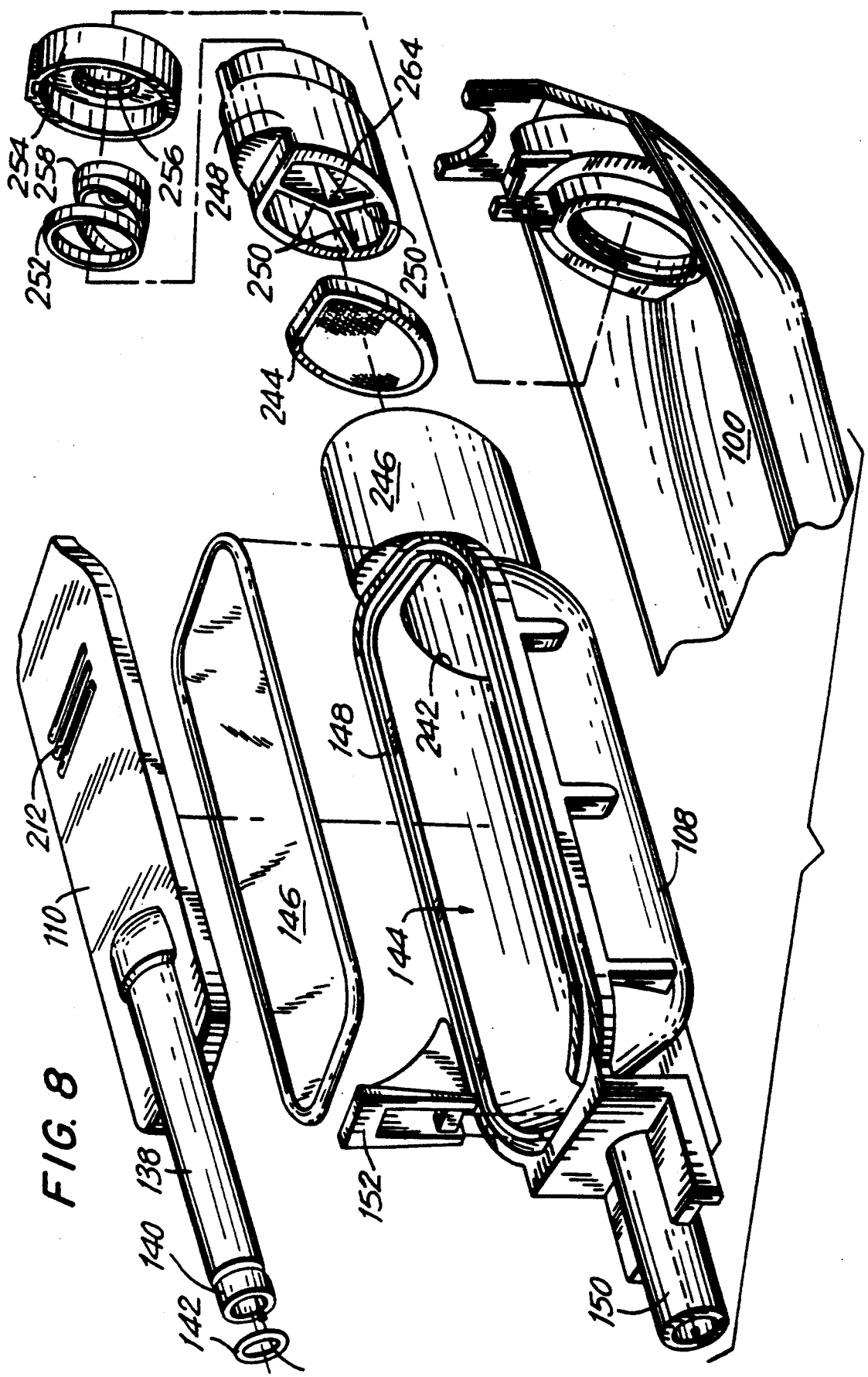
FIG. 8 is an elevated perspective, exploded view of a third portion of the handpiece.

The handpiece 24, cumulatively shown in the exploded perspective partial views of FIGS. 6 to 8, is formed of a multiplicity of housing sections that are configured so as to individually and collectively define a variety of passages, conduits and channels for communication of the pulsed treatment liquid, and of a flowable medicament or additive for mixture with the treatment liquid, between the handpiece inlet and an appliance or tip element or the like mounted dependingly at the handpiece outlet. An outer casing 96, composed of a top shell 98 (FIG. 6) and a bottom shell 100 (FIG. 8) that are secured together as, for example, by screws or the like, surrounds and encloses the various operating parts and elements of the handpiece 24 and is preferably contoured to provide both an aesthetically pleasing appearance and a hand-held, readily graspable and manually manipulatable unit for use and movement in general proximity to the user's mouth. The major housing sections of the handpiece 24, in the embodiment of the inventive oral irrigator herein disclosed, are a main body 102, a bottom manifold 104, a top manifold 106, and a medicament tank body 108 and associated tank cover member 110. These elements variously and cooperatively interengage in the manner shown in and apparent from the drawings.

The main body 102 carries a tubular extension 112 forming an inlet mount to which the flexible hose 26 is secured for communicating the pulsatile stream of treatment liquid from the shower head adapter 22 to the handpiece 24. A strain relief cap or coupling 114 may also be provided about the hose 26 at and proximate its securement to the extension 112. The arrow 116 (FIG. 7) represents the direction of pulsatile liquid flow into the handpiece.

As delineated by the arrow 118 in FIG. 7, from the inlet 112 the incoming pulsatile liquid stream is directed downwardly through the main body 102 to the lefthand end (in FIG. 7) of the bottom manifold 104. There, as indicated by the arrow 120, the incoming stream is bifurcated or split into a primary stream that continues to flow in a direction generally axially along the elongated manifold 104 and a secondary stream that is laterally diverted into a substantially parallel channel 122. The secondary stream, as will hereinafter become apparent, is utilized for the controlled dispensing of a stored flowable medicament into the primary stream at a relatively constant, dynamically-adjusted volumetric ratio of medicament to treatment liquid. The resulting pulsatile mixture is then discharged from the handpiece through the appliance head or tip 32 or like appendage mounted at the output end of the outer casing 96 for use in oral irrigation or related procedures.

Figure 9:
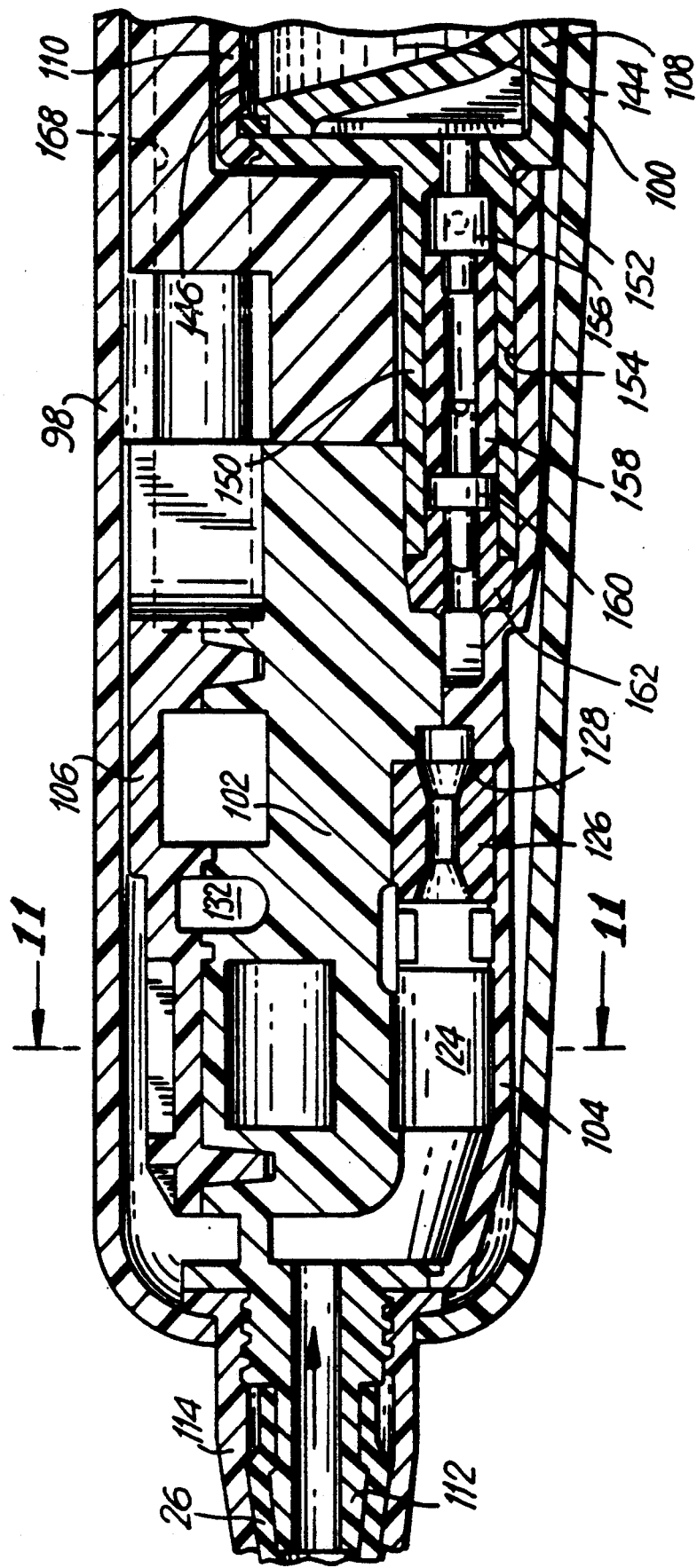
FIG. 9 is a sectional view, partly broken away, taken along the lines 9—9 in FIG. 1.

The primary pulsed liquid stream is first directed into and through a conventional pressure-reducing check valve 124 that operatively provides an inlet-to-outlet pressure reduction of, in the currently preferred embodiment, approximately one-half pound per square inch (⅛ psi) and, in addition, prevents reverse liquid flow therethrough. The check valve 124 may, by way of example, be implemented by a ⅛-inch "Smart Valve", Part No. WQ110FDA which is commercially available from Smart Products of San Jose, Calif. The reduced-pressure stream from the valve 124 is then fed into and through a generally tubular orifice reducer 126 which, in the currently preferred embodiment of the invention, has a cross-sectional flow path diameter of approximately 0.085 inches. Both the check valve 124 and the orifice reducer 126 are supportedly seated in a suitably configured, laterally-arcuate cutout defined in the bottom manifold 104 and, if desired or otherwise deemed appropriate, conformingly in the opposed wall of the main body 102, with the outlet end of the reducer 126 positioned in abutment with a positioning wall 128 (FIG. 7) of the bottom manifold. As further seen in FIG. 9, the outlet end of the valve 124, illustrated as generally frustoconical in FIG. 7, is slightly spaced from the inlet end of the flow reducer 126 along the longitudinal elongation of the bottom manifold cutout.

From the orifice reducer outlet, the primary pulsatile flow of treatment liquid is directed upwardly (in the FIG. 7 orientation), as indicated by the arrow 129, through a generally vertical feed bore 130 defined in the main body 102 and opening, at its top, into the far end (in FIG. 7) of a laterally-extending liquid crossover passage 132. The location of the lower end or entry part of the feed bore 130 relative to the bottom manifold 104, when the bottom manifold is fitted to the main body 102 in the assembled form of the handpiece 24, is shown in phantom in FIG. 7. That broken-line, phantom depiction of the lower end of the feed bore 130 also indicates, as will hereinafter be apparent, the general location of a mixing chamber at which concentrated medicament is added to and combined with the primary liquid stream just prior to its communication to and through the bore 130.

Returning now to the secondary stream of pulsed treatment liquid, from the righthand end (in FIG. 7) of the bottom manifold channel 122 the stream is directed upwardly into and through a generally vertically-oriented aperture 134 (not directly visible in FIG. 7) defined in the main body 102 and terminating, at its top end, within a cavity 136 of the main body. The medicament tank cover member 110 carries a rearwardly outwardly extending inlet tube 138, the free end 140 of which is seated, in conjunction with an O-type sealing ring or grommet 142 or the like, in the cavity 136. The tube 138 circumferentially bounds an elongated tubular conduit for the secondary pulsatile liquid stream and terminates along the underside or bottom surface of the cover 110 in opposition to the medicament storage reservoir 144 that is defined by the tank body 108. Thus, the secondary stream is directed, through the tube 138, to the underside of the cover member 110 through one or a plurality of suitably-sized openings (not shown) communicating with the tube-defined conduit and, where multiple openings are provided, spaced along at least a portion of the longitudinal extension of the cover member 110.

A resiliently elastic or deformable membrane or diaphragm 146 extends coextensively with and across the top of the medicament storage reservoir and is held in captive relation between the top rim 148 of the tank body 108 and the correspondingly contoured edge portion of the overlapping tank cover 110 when the cover is seated on the body in the assembled condition of the handpiece 24. The diaphragm 146 thereby boundingly defines, in conjunction with the opposed inner face of the tank cover 110, an expansion chamber located immediately adjacent the reservoir 144 and separated by and sharing the common diaphragm-formed wall for receiving the secondary pulsatile liquid stream that is fed through the inlet tube 138. The diaphragm 146 thus functions as a displacement bladder that is resiliently expandable, as it fills with liquid from the secondary stream entering through the tank cover inlet tube 138, into the interior expanse of the reservoir 144 to thereby increase the pressure on medicament therein stored and cause a discharge of stored medicament, in direct volumetric relation to the expansion of the diaphragm, through an outlet tube 150 communicating with the reservoir and integrally depending from the tank body 108. The tank body 108 may also optionally carry or include, at or proximate the entrance to the tubular outlet 108, an entry-constricting anti-herniation member 152 for preventing unintended elastic expansion of the diaphragm 146 into the outlet entrance, an effect which could potentially rupture or otherwise damage the diaphragm.

The medicament tank body outlet tube 150 is supportedly received and seated in a correspondingly sized and contoured recess 154 defined in the bottom manifold 104. From the tube 150, the flowable medicament discharged from the reservoir 144 is directed serially through a one-way or check valve 156, a connecting tube 158, a flow or orifice reducer 160, and a flow-through end cap connector element 162. In the currently preferred embodiment of the invention, the flow passage cross-sectional diameter of the flow reducer 160 is approximately 0.02 inches. As indicated by the arrow 164, the discharged medicament from the end cap connector 162 enters the so-called mixing chamber located immediately below the feed bore 130 and at which the medicament mixes and combines with the primary pulsatile stream of treatment liquid. The resulting mixture of treatment liquid and medicament advances upwardly through the main body feed bore 130, into the far (in FIG. 7) end of the crossover passage 132 and, as reflected by the arrow 166, into an elongated outflow conduit 168 (FIG. 6) that is seated, at its intake end, within a suitably arcuate concavity 170 of the main body 102. The intake end of the outflow conduit 168 may also, to facilitate its liquid-tight receipt and mounting in the concavity 170, carry an end-mounted nipple 172 and an O-type sealing ring or grommet 174 or the like.

The outlet end of the outflow conduit 168, seen to the right in FIG. 6, connects to a forward connector element 176 that is positionally secured (FIG. 10) between the top and bottom shells 98, 100 of the handpiece outer casing 96. The element 176 provides a seat for a front bushing 178, also captured between the top and bottom casing shells and to which working appliance heads—as, for example, the tapered irrigating tip 32 illustrated in FIG. 1, or such other appliances as an irrigating toothbrush or other specialized tips and the like—are releasably mountable. Toward this end, an O-ring 180 or the like may be disposed in captured relation between the connecting element 176 and bushing 178 to thereby define a resiliently deformable, inwardly-projecting annular rib for snap-fit and releasable engagement with a grooved finger-like adapter 182 (FIG. 10) carried at the rearward end of the irrigating tip 32 and other similarly-engageable appliance heads.

Each appliance tip or head will also, as should be evident, include a passage defined therewithin and extending from its finger-like adapter 182 to or proximate its distal or work end for communicating outflow conduit-delivered pulsed treatment liquid from the element 176 and bushing 178 to the distal end of the appliance.

The handpiece 24 further includes, in one preferred form of the inventive device, user-manipulatable controls for selective adjustment of the rate of volumetric discharge or outflow, through a depending appliance head or tip 32, of pulsed treatment liquid (with or without medicament), and/or for selective "on-off" switching control of medicament dispensing from the storage reservoir 133 for mixture at a predetermined volumetric ratio with the incoming primary stream of water or other treatment liquid, the resulting mixture to be discharged from the handpiece. As shown in FIGS. 6 and 12, this functionality is respectively implemented, in the oral irrigator 20, by a main flow regulator 184 and a medicament flow regulator 186, both of which are selectively and reciprocatably displaceable in a direction oriented longitudinally along the handpiece 24.

Each of the regulators 184, 186 is formed as an elongated member having a piston portion 188, 190 and an adjustment portion 192, 194, respectively, at its opposite ends. The adjustment portions 192, 194 each respectively carry an upstanding boss 196, 198 for captive engagement with a finger-movable slide switch 200, 202 that is reciprocatable along a longitudinally-oriented recess 204, 206 defined in the handpiece casing top shell 98. Projecting keys or teeth 208, 210 on the regulator portions 192, 194 are engageable with a series of substantially parallel detents 212 on the adjacently-disposed medicament tank cover member 110 to cooperatively delineate a multiplicity of serial click stops for facilitating positional adjustment and retention of the selected displacements of the slide switches 200, 202 and regulator members 184, 186.

The main flow regulator piston 188 is provided with a plurality of annular grooves 212 into which O-type sealing rings or grommets 214 are receivable to separate and define a multiplicity —two in the disclosed embodiment—of piston sections, herein delineated a control section 216, diametrically through which an elongated through-passage 218 extends, and a blocking section 219. The piston 188 is axially slidable within and along a bore 220 defined in and longitudinally along the main body 102 (see FIG. 12) and sized so as to provide for substantially liquid-tight abutment of the O-rings 214 against the interior periphery of the bore 220. As will now be described, user-initiated longitudinal displacement of the regulator 184, and thus of the piston 188 along the bore 220, results in selective variation and adjustment of the volumetric flow rate of pulsed treatment liquid that is discharged from the forward end of the handpiece 24 through the applicator tip 32.

The feed bore 130 has heretofore been described as providing a generally vertical path defined within the main body 102 and along which the primary pulsatile liquid stream—typically but, in fact, optionally mixed with medicament from the storage reservoir 144 at a predetermined, substantially constant ratio—flows from the mixing chamber of the bottom manifold 104 to the outflow conduit 168. In a preferred form of the handpiece 24, however, the feed bore 130 is formed as two separate parts or sections which, rather than being mutually aligned, are spaced longitudinally apart from each other along the main body 102 and, more particularly, axially along the piston bore 220. Thus, the lower portion of the feed bore 130 extends from the bottom manifold mixing chamber into the piston bore 220 and the upper portion of the feed bore 130 extends from the piston bore 220 into the crossover passage 132, the two feed bore portions and the piston bore 220 together forming a jog or dogleg-like path for the pulsatile treatment liquid. With the main flow regulator 184 in its "off" or "no flow" position—i.e. fully to the left in FIG. 6 or down in FIG. 1—the sealing ring 214 located between the control and blocking sections 216, 219 of the piston 188 is situated in the piston bore 220 between the spaced apart upper and lower portions of the feed bore 130 and thereby blocks liquid flow between the two feed bore sections. Accordingly, in this first position of the main flow regulator 184, no pulsatile treatment liquid can pass from the bottom manifold mixing chamber to the outflow conduit 168 for discharge through the appliance head or tip 32.

As the regulator 184 is, on the other hand, advanced in the direction of and to its "on" or "full flow" position—i.e. to the right in FIG. 6 or up in FIG. 1—an increasing portion of the through-passage 218 extends between the doglegged upper and lower portions of the feed bore 130 and a correspondingly increasing flow volume of pulsatile treatment liquid is delivered upwardly through the main body 102 and into the outflow conduit 168 for delivery to and through the appliance head or tip 32. Suitable sizing and shaping of the upper and/or lower portions of the feed bore 130, and/or of the through-passage 218, can be utilized for further smoothing and enhancing the adjustability of the outflow of treatment liquid between the fully "off" and fully "on" positions of the regulator 184. Indeed, maximum efficiency in achieving smoothly-graduated control of the volumetrically-adjustable outflow of treatment liquid as the main flow regulator 184 is selectively displaced can be realized by implementing the lower portion of the feed bore 130 as a plurality of discrete, parallel apertures—as for example three such apertures in a particularly preferred form of the inventive irrigator 20—which are spaced apart along the longitudinal extension of the piston bore 220; as the regulator 184 is advanced toward its "on" or "full flow" position, the piston through-passage 218 aligns with a gradually increasing number of the apertures that collectively form the lower portion of the feed bore 130 and, thereby, permit a gradually-increasing volume of treatment liquid to flow upwardly through the main body 102 and into the outflow conduit 168 for delivery to and through the appliance head 32.

The medicament flow regulator 186 is structured and functions in a similar manner. Its piston 190 is divided into a plurality of sections separated by O-type sealing rings 222 that are seated in annular grooves 224; those piston sections include a central control section 226, which is provided with a diametrically extending through-passage 228, and blocking sections 230, 232 located on opposite sides or ends of the control section. The regulator piston 190 is also axially slidable within and along a piston bore 234 (see FIG. 12) that is defined in and longitudinally along the main body 102, the bore 234 being sized for a substantially liquid-tight interference fit between each of the sealing rings 222 and the interior wall of the piston bore.

Here, too, a preferred form of the aperture 134—through which the secondary stream of pulsed liquid is fed from the channel 122 of the bottom manifold 104 to the medicament tank cover inlet tube 138 for resiliently expanding the diaphragm 146—consists of unaligned lower and upper sections (not shown) that, in conjunction with the piston bore 234, form a jog or dogleg-like path for the secondary stream. Thus, the lower portion of the aperture 134 extends upwardly from the rightmost (in FIG. 7) end of the secondary stream channel 122 into the piston bore 234, and the upper portion of the aperture 134 extends downwardly from the cavity 136 into the bore piston 234 at a location spaced longitudinally along the main body 102 (and axially along the bore 234) from the lower portion of the aperture.

With the medicament flow regulator 186 shifted to its "off" or "no flow" position—i.e. fully to the left in FIG. 6 or down in FIG. 1—the sealing ring 222 between the control section 226 and blocking section 232 of the regulator piston 190 is located in the piston bore 234 between the upper and lower portions of the aperture 134. In this first position of the regulator 186, therefore, that sealing ring 222 blocks liquid flow between the upper and lower portions of the aperture 134 and, thereby, from the secondary stream channel 122 to the tank cover inlet tube 138. Since the secondary stream of treatment liquid is blocked by the piston-carried sealing ring 222 from reaching the inlet tube 138, medicament is not forcibly discharged, by secondary stream deformation of the diaphragm 146, from the storage reservoir 144 for mixture with the primary stream of pulsed treatment liquid.

With movement of the regulator member 186 in the direction of and to its "on" or "full flow" position—i.e. to the right in FIG. 6 and up in FIG. 1—the through-passage 228 is displaced so that it extends spanningly between the doglegged upper and lower portions of the aperture 134 and defines a dogleg flow path from the lower to the upper portions of the aperture 134, whereby the secondary stream of treatment liquid is delivered upwardly through the main body 102 and into the inlet tube 138 for delivery to the expansion chamber defined between the diaphragm 146 and tank cover 110. The diaphragm, elastically deformed by the secondary pulsatile stream entering the expansion chamber, thereby expands into the reservoir 144 and applies increased pressure to its contents to force the stored medicament outwardly from the reservoir through the outlet tube 150 and into admixed combination with the primary pulsatile stream at the bottom manifold mixing chamber.

In another preferred form of the inventive oral irrigator 20, one or more of the through-passage 228 and the upper and/or lower portions of the aperture 134 may, as with the main flow regulator 184, be suitably contoured, sized, shaped and otherwise defined to optionally provide—in place of simple "on-off" control in the addition of stored medicament to the primary pulsatile stream of treatment liquid—effective gradual or graduated adjustability of the resulting ratio of medicament to treatment liquid as the regulator 186 is displaced between its fully "off" and fully "on" positions. In one currently contemplated arrangement for enabling user-adjustability of the relative volume of medicament to be mixed with the primary treatment liquid stream, the lower portion of the aperture 134 may be implemented as a plurality of discrete, parallel bores that are spaced apart along the logitudinal extension of the medicament piston bore 234. With such an arrangement of multiple spaced apart bores forming the lower portion of the aperture 134, advancement of the regulator 186 from its fully "off" toward its "on" position carries the through-passage 228 into aligned relation with a sequentially increasing number of those bores and, thereby, provides step-like increases in the volume of the secondary pulsatile stream which is flowable upwardly through the through-passage 228 and the upper portion of the aperture 134 for delivery to the diaphragm expansion chamber. Suitable sizing and shaping of the multiple bores can minimize and effectively eliminate discontinuities in the volumetric outflow of medicament and thereby further smooth and enhance the selective adjustability of the forced volumetric and ratiometric outflow of stored medicament through user-effected movement of the regulator 186 between its fully "off" and fully "on" positions.

The medicament flow regulator 186 provides still further functionality in the currently-preferred form and operability of the herein-disclosed embodiment of the inventive oral irrigator. This additional functionality enables the discharge or release of accumulated diaphragm-deforming liquid from the region between the diaphragm 146 and the tank cover 110 after one's use of the device 20 has been completed and both the medicament regulator 186 through user-manipulation of the slide switch 202, and the main flow regulator 184 through user-manipulation of the slide switch 200, have been returned to their respective initial or "off" positions. For this purpose, a drainage aperture 236 defined in the main body 102 extends between the near (in FIG. 7) end of the crossover passage 132 and the medicament flow piston bore 234 (FIG. 12). In addition, the medicament regulator piston through-passage 228 is longitudinally sized so as to extend spanningly between the drainage aperture 236 and the upper portion of the aperture 134 and thereby define a liquid communication path between those apertures when the regulator 186 is located in its "off" position.

Thus, when the medicament flow regulator 186 is located in displaced relation to its fully "off" position—i.e. when the regulator 186 is positioned so as to add stored medicament to the primary pulsatile stream—the sealing ring 222 located between the control section 226 and the blocking section 230 of the piston 190 is disposed, in the bore 234, between the drainage aperture 236 and the upper portion of the secondary stream aperture 134. When thus positioned between the respective junctures of the piston bore 234 with each of the apertures 236 and 134, that sealing ring 222 blocks all liquid flow from one aperture to the other and, most particularly, from the upper portion of the aperture 134 to the drainage aperture 234. The secondary pulsatile stream, as described hereinabove, is accordingly directed from the bottom manifold channel 122, through the lower and then upper portions of the aperture 134, through the inlet tube 138, and into the region between the tank cover 110 and the diaphragm 146 whereby the diaphragm is elastically deformed to apply medicament-discharging pressure to the interior of the storage reservoir 144 and thereby effect an outflow of medicament therefrom for mixture with the primary pulsatile stream of treatment liquid.

When, on the other hand, the medicament flow regulator 186 is subsequently returned to its fully "off" position, the through-passage 228 of the control section 226 of the piston 190 is located coincident with and spans the openings, in the piston bore 234, of the drainage aperture 236 and the upper portion of the aperture 134. This arrangement thereby defines an annular liquid flow passageway between the drainage aperture 236 and the upper portion of aperture 134. It will also be recalled that, in the "off" position of the regulator 186, the liquid pathway between the lower and upper portions of the aperture 134 is blocked or closed by the sealing ring 222 carried between the control section 226 and the blocking section 232 of the regulator piston 190, so that no additional secondary stream liquid can flow into the tank cover inlet tube 138 for membrane-deforming delivery to the diaphragm 146. In any event, as should now be apparent the through-passage 228 in the piston control section 226 provides, from and between the drainage aperture 236 and the upper portion of the aperture 134, a drainage flow path for membrane-deforming liquid that remains between the tank cover 110 and the diaphragm 146 when the medicament regulator 186 is returned to its fully "off" position. That liquid accordingly flows, driven by the return urgency of the liquid-deformed, resiliently elastic diaphragm 146, outwardly through the tank cover tube 138, downwardly through the upper portion of the aperture 134, along the piston blocking section 230, upwardly through the drainage aperture 236, along the crossover passage 132, into and through the outflow conduit 168, and into and through the appliance tip 32 for discharge from the handpiece 24. With the presence and pressure of that remaining secondary stream liquid on the diaphragm removed—i.e. when both the main and medicament flow regulators 184, 186 are located at their fully "off" positions—the diaphragm returns to its initial unstressed, undeformed, relatively flat condition between the tank cover member 110 and the medicament storage reservoir 144. As explained hereinafter, the resilient return of the diaphragm 146 from its deformed to its initial, substantially unstressed condition is further facilitated by the permitted entry of ambient air into the reservoir 144 to replace the discharged volume of medicament and thereby prevent the development of a partial vacuum or negative pressure within the storage reservoir as the elastically-expanded diaphragm recedes.

A particularly preferred form of the inventive oral irrigator device 20 may further incorporate a suitable arrangement for assuring that the medicament flow regulator 186 cannot be advanced from its "off" position unless or without prior or concurrent displacement of the main flow regulator 184 from its "off" or "no flow" position. This functionality—for the purpose of preventing a secondary stream-driven discharge of stored medicament without its being ratiometrically mixed with a suitable flow of treatment liquid—can be provided in any of a number of ways as a general matter of design choice. For example, the medicament flow slide switch 202 may carry a fixed rod or other elongated member (not shown) projecting outwardly from the switch 202 into a slot defined in the main flow slide switch 200 and extending in the longitudinal direction of the handpiece 24. Through suitable placement of the fixed rod and slot, such an arrangement enables independent displacement of the main flow switch 200 from its "off" position without requiring concurrent movement of the medicament flow switch 202—the fixed rod simply sliding within and along the slot—while requiring or causing the main flow switch to be moved from its "off" position, through abutment of the fixed rod with one end of the slot, in order to permit like displacement of the medicament flow switch from its "off" position.

Another way of accomplishing this partially interlocked functionality of the regulators 184, 186 is by suitably sizing the lengthwise extensions of the opposing actuation tabs 238, 240 that are carried, respectively, on the main and medicament flow regulators 184, 186. For this purpose, the tabs 238, 240 are sized so that their free ends overlap or, put another way, so that the tabs are movable into interfering abutment with each other as the regulators are variously displaced. In such an arrangement, with both regulators 184, 186 in their fully "off" positions (i.e. to the left in FIG. 6), the tab 240 of medicament flow regulator 186 is located immediately rearward (to the left in FIG. 6) of and, most preferably, in abutment with the tab 238 of the main flow regulator 184. This permits independent and unencumbered forward (rightward) displacement of the main flow regulator 184, so as to gradually increase the outflow of pulsed treatment liquid from the appliance tip 32, without regard to the position of the medicament flow regulator 186 Forward (rightward) movement of the medicament regulator from its fully "off" position, on the other hand, requires prior or concurrent forward (rightward) displacement of the main flow regulator 184 since the medicament regulator tab 240 is unable to advance forwardly past the main flow regulator tab 238. Thus, displacement of the regulator 186 to provide for the mixing of medicament with the pulsatile treatment liquid requires that the main flow regulator 184 be at least concurrently displaced from its "off" position. And where the oral irrigator 20 is optionally configured so as to permit user-adjustment of the ratio of medicament to be mixed with the treatment liquid, selective increases in the amount of medicament to be dispensed from the work or appliance-carrying end of the handpiece 24 requires corresponding increases in the volume of treatment liquid with which the medicament is mixed and for discharge from the handpiece. Similarly, return displacement of the main flow regulator 184 to its fully "off" position automatically carries with it—through interfering abutment of the tabs 238, 240—the medicament flow regulator 186 which is correspondingly returned to its fully "off" position.

Figure 10:
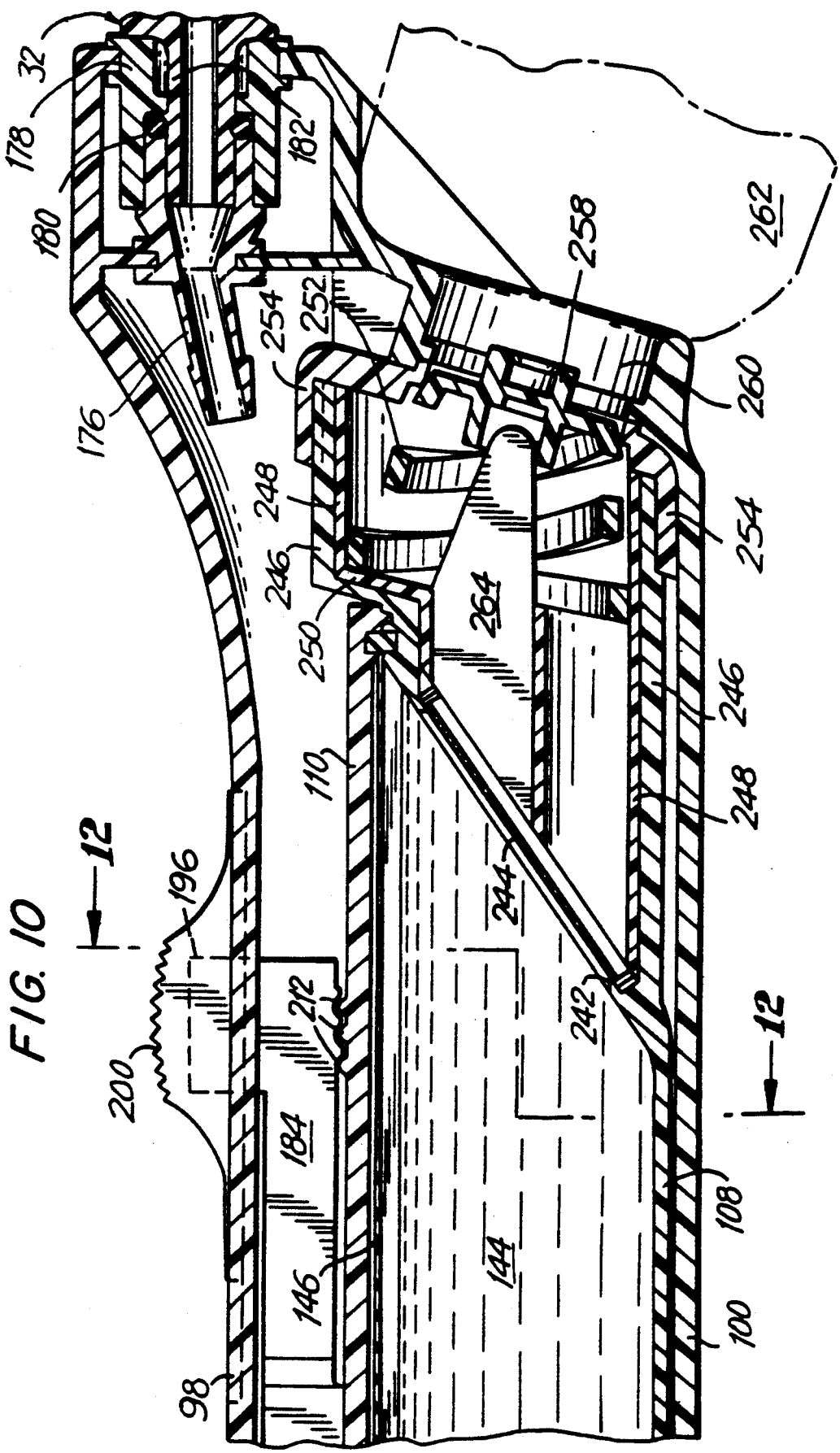
FIG. 10 is a sectional view, partly broken away, taken along the lines 10—10 in FIG. 1.

With reference now to FIGS. 8 and 10, the medicament tank body 108 is provided at its front or forward end with a fill opening 242 through which medicament may be added to the storage reservoir 144 as and when necessary or desired. An inlet screen 244 disposed in and coextensive with the fill opening 242 is effective both to deter the inadvertent introduction of particulate impurities into the medicament reservoir 144 and to avert secondary pulsatile stream-driven elastic expansion or herniation of the diaphragm 146 into or through the opening 242. An integrally-formed or carried elongated collar 246 that surrounds the screened fill opening 242 and projects from the forward end of the tank body 108 provides a receiving housing for a spring retainer member 248. The rearward end of the retainer member 248 includes a series of ribs or struts 250 that define a support for a spring member 252 which is captured between the ribs and a cap element 254. An opening 256 in the cap element 252 provides a liquid-tight valve seat for a boss-like valve member 258 carried on the forward end of spring 252. Thus, the urgency of the spring member 252 presses the spring-carried valve member 258 against the periphery of the cap element opening 256 to normally provide a liquid-tight seal between the valve member 258 and valve seat-defining opening 256 against unintended outflows or leakage of stored medicament through the opening 256. At the same time, the spring force of the spring member 252 is selected so as to permit sufficient inward displacement of the valve member 258 from the periphery of the opening 256 to permit ambient air to enter the reservoir 144, through the opening 256, as the diaphragm 146 recedes from its elastically-deformed condition when the medicament flow regulator 186 is returned to its "off" position following use of the oral irrigator device 20.

When the valve member 258 is inwardly depressed by an externally-applied force to fill or refill the reservoir 144 with medicament—as, for example, by a conformingly-configured tip or nozzle 260 carried on a bottle or container 262 of medicament that is movable into adjacency and abutment with the forward end of the outer casing 96 (see FIG. 10)—the separation of the valve member and circumferential lip or periphery of the opening 256 permits an inward flow of medicament through the retainer member 248 and screen 244 and into the reservoir. Upon removal or abatement of the inwardly-directed external force that is applied to the valve member 258, the spring 252 provides the return urgency for restoring the valve member into liquid-tight sealing relation with the peripheral edge or lip of the opening 256, thereby closing the valve and preventing loss of medicament from the reservoir. The retaining member 248 may also carry a generally axially-extending centering pin or post 260 to positionally maintain the spring 252 within the retainer member 252, and the valve member 258 in proper registration alignment with the opening 256, as the spring is operatively compressed and expanded.

A particularly important and advantageous operative feature of the inventive oral irrigator device 20 lies in the ability to mix a stored medicament with the treatment liquid for discharge from the device at a notably constant and dynamically-adjusted volumetric ratio of medicament to treatment liquid. The ability to do so results from a variety of structural and operational aspects of the inventive device, one of which is the use of an expandable diaphragm 146 for applying an evenly distributed force to the contents of the reservoir 144 to evenly eject a force-related flow of the stored medicament through the tank body outlet tube 150 for mixture with the primary pulsatile stream. Expansion of the diaphragm, it will be recalled, is effected by the secondary pulsatile stream which is fed to and volumetrically enlarges—as a function of the pressure of the secondary stream—the expansion chamber that is bounded by the diaphragm and the tank cover 110. Since both the primary and the secondary pulsatile streams are derived from the same pulsating treatment liquid flow that enters the handpiece 24 through the flexible hose 26, the pressure of the secondary stream dynamically tracks the pressure of the primary stream. Consequently, the volume of medicament being discharged from the reservoir 144 by the secondary stream pressure dynamically varies in accordance with the pressure—and, correspondingly, the flow—of the primary stream with which it is mixed, thereby fully and rapidly responding to fluctuations or changes in the primary stream flow rate and maintaining a substantially constant volumetric ratio of medicament to treatment liquid in the resulting mixture.

Further assuring ratiometric consistency in the medicated treatment liquid mixture is the deliberate creation of a pressure differential between the primary pulsatile liquid stream that is directed for discharge from the device and the secondary pulsatile liquid stream that forcibly drives medicament from the storage reservoir for mixture with the primary stream, in combination with the ratio of flow passage constrictions in the primary pulsatile stream (by way of the orifice reducer 126) and in the output stream of stored medicament from the reservoir 144 (by way of the orifice reducer 160). In the herein-disclosed embodiment, the pressure differential is developed by the pressure reducing check valve 124 that is disposed in the path of the primary pulsatile stream so as to reduce the primary stream pressure, by approximately $\frac{1}{4}$ psi in the currently-preferred device 20, relative to the secondary stream pressure. Pressure differentials in the range of approximately $\frac{1}{4}$ to approximately 1 psi are also within the generally contemplated utility of the invention. The relatively higher pressure of the medicament that is forcibly discharged from the reservoir 144 by the secondary pulsatile stream, with respect to the pressure of the primary stream with which the medicament is presented for mixture, effectively avoids the development of backpressure or other obstructions or impediments to mixing that could create unintended and uncontrolled variations in the ratio of medicament to treatment liquid in the resulting mixture.

There has accordingly been disclosed, in this specification, an oral irrigator device constructed in accordance with and providing the multiple features and advantages of the present invention. The inventive device is powered and operated entirely by the incoming continuous-flow stream of treatment liquid from the liquid supply line with no other connection to external sources of power. It includes an adapter that is easily installed between the water supply or feed pipe and a shower head for generating a pulsatile stream from the continuous-flow stream of water, and a user-manipulatable handpiece connected to the adapter by a flexible hose for selectively directing the discharged pulsatile flow into association with the user's mouth. The device further provides the unique and particularly advantageous ability to mix, with the pulsatile liquid stream, a stored medicament at a ratio of medicament to treatment liquid that is dynamically maintained with unusual consistency and, optionally, which may be readily adjusted by the user.

While there have been shown and described and pointed out fundamental novel features of the invention as applied to a preferred embodiment thereof, it will be understood that various omissions and substitutions and changes in the form and details of the device illustrated, and in its operation, may be made by those skilled in the art without departing from the spirit of the invention. It is the intention, therefore, to be limited only as indicated by the scope of the claims appended hereto.

What is claimed is:

1. In a device for operatively discharging a pulsating flow of a medicated treatment liquid,
   conversion means for receiving a variable rate stream of a continuous flow treatment liquid and for generating, from said continuous flow stream, a pulsating stream of the treatment liquid at an operating pressure;
   means for dividing said pulsating stream into a primary pulsatile stream and a secondary pulsatile stream of the treatment liquid;
   means for creating a pressure differential between said primary and secondary pulsatile streams so that said primary stream has a first pressure and said secondary stream has a second pressure;

tank means defining a reservoir for storing a medicament for mixture with the treatment liquid and having an outlet for communicating treatment liquid from said reservoir to said primary pulsatile stream of treatment liquid for mixture therewith;

actuating means for applying a predeterminately-variable force to said tank means so as to discharge medicament from said reservoir through said reservoir outlet at a volumetric rate substantially proportional to said force for mixture with the primary pulsatile stream of treatment liquid;

means for directing said secondary pulsatile stream of treatment liquid to said actuating means for generating said force as a function of the second pressure of said secondary pulsatile stream; and means for mixing the discharged medicament from said reservoir outlet with said primary pulsatile stream at a relatively constant volumetric ratio of medicament to treatment liquid to define a pulsating flow of a medicated treatment liquid for discharge from the device.

2. In a device in accordance with claim 1, said actuating means comprising a chamber defined adjacent said reservoir for receiving said secondary pulsatile stream, and a flexible member forming a wall of said chamber and disposed between said chamber and reservoir for flexible expansion into said reservoir as the secondary stream is received in said chamber to thereby apply said medicament-discharging force to said tank means.

3. In a device in accordance with claim 1, said conversion means comprising a turbine mounted for rotation by said continuous flow stream of treatment liquid and including an aperture defined through said turbine, and means for directing said continuous flow stream into repeatedly-interrupted communication with said aperture to create said pulsating liquid flow as the continuous flow treatment liquid interruptedly passes through said aperture during rotation of said turbine.

4. In a device in accordance with claim 1, said pressure differential creating means comprising reducing means through which the primary pulsatile stream is directed for reducing the pressure of the primary pulsatile stream relative to the pressure of the secondary pulsatile stream.

5. In a device in accordance with claim 4, wherein the primary pulsatile stream is directed through said reducing means upstream of said mixing means.

6. In a device in accordance with claim 4, wherein said reducing means reduces the pressure of the primary pulsatile stream by approximately one-half psi.

7. In a device in accordance with claim 4, wherein said pressure differential between the primary and secondary pulsatile streams is approximately one-half psi.

8. In a device in accordance with claim 1, further comprising means for normalizing the pulsating stream of treatment liquid from said converting means.

9. In a device in accordance with claim 1, further comprising a user-graspable hand-held housing having a discharge outlet from which said medicated treatment liquid is discharged, said tank means and said actuating means being disposed in said housing.

10. In a device in accordance with claim 9, further comprising an adapter mounted to a source of said continuous flow treatment liquid, said conversion means being disposed in said adapter, and conduit means connecting said adapter and housing for communicating said pulsating liquid stream from said adapter to said housing.

11. In a device in accordance with claim 10, said dividing means and said mixing means being disposed in said housing.

12. In a device in accordance with claim 1, further comprising first adjustable means operable for controllably varying the volumetric ratio of medicament to treatment liquid in said medicated treatment liquid by selectively varying the volumetric flow of the secondary pulsatile stream to said actuating means so as to correspondingly vary the force applied to said tank means and, thereby, the volumetric rate of medicament discharge through said reservoir outlet for mixture with the primary pulsatile stream.

13. In a device in accordance with claim 12, further comprising second adjustable means operable for selectively varying the volumetric flow rate of said medicated treatment liquid for discharge from the device and disposed downstream of said mixing means.

14. In a device in accordance with claim 1, further comprising adjustable means operable for selectively varying the volumetric flow rate of said medicated treatment liquid for discharge from the device and disposed downstream of said mixing means.

15. In a device in accordance with claim 14, further comprising switch means operable for selectively discontinuing said discharge of medicated treatment liquid from said reservoir for mixture with the pulsatile stream of treatment liquid.

16. In a device in accordance with claim 1, said dividing means further comprising means for predeterminately limiting volumetric flow of the primary pulsatile stream by defining a cross-sectionally reduced aperture through which the primary pulsatile stream is flowable.

17. In a device in accordance with claim 1, said mixing means further comprising means for predeterminately limiting volumetric flow of the discharged medicament for mixture with the primary pulsatile stream by defining a cross-sectionally reduced aperture through which the discharged medicament is flowable.

18. In a device in accordance with claim 1, said dividing means further comprising first means for predeterminately limiting volumetric flow of the primary pulsatile stream by defining a cross-sectionally reduced first aperture through which the primary pulsatile stream is flowable, and said mixing means further comprising second means for predeterminately limiting volumetric flow of the discharged medicament for mixture with the primary pulsatile stream by defining a cross-sectionally reduced second aperture through which the discharged medicament is flowable, said cross-sections of first and second apertures having a predetermined relationship selected to facilitate mixing of the discharged medicament and the primary pulsatile stream of treatment liquid at said mixing means.

19. In a device in accordance with claim 18, said first aperture having a cross-sectional diameter of approximately 0.085 inches and said second aperture having a cross-sectional diameter of approximately 0.020 inches.

* * * * *